US009642954B2

(12) United States Patent
Mormino et al.

(10) Patent No.: US 9,642,954 B2
(45) Date of Patent: *May 9, 2017

(54) REDUCED-PRESSURE SYSTEM AND METHOD EMPLOYING A GASKET

(71) Applicant: KCI Licensing, Inc., San Antonio, TX (US)

(72) Inventors: Richard Paul Mormino, San Antonio, TX (US); Todd Matthew Fruchterman, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/135,754

(22) Filed: Apr. 22, 2016

(65) Prior Publication Data

US 2016/0235896 A1 Aug. 18, 2016

Related U.S. Application Data

(62) Division of application No. 14/025,271, filed on Sep. 12, 2013, now Pat. No. 9,345,823, which is a division
(Continued)

(51) Int. Cl.
*A61F 13/00* (2006.01)
*A61M 1/00* (2006.01)
(Continued)

(52) U.S. Cl.
CPC ..... *A61M 1/0088* (2013.01); *A61F 13/00068* (2013.01); *A61F 13/0216* (2013.01);
(Continued)

(58) Field of Classification Search
CPC ............ A61M 1/0088; A61F 13/00068; A61F 13/0216; A61B 17/085; A61B 2017/005; A61B 19/08; A61B 2019/085
See application file for complete search history.

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Tatyana Zalukaeva
*Assistant Examiner* — Benjamin Klein

(57) ABSTRACT

A reduced-pressure treatment system for treating a tissue site on a patient includes a gasket releasably attached around a perimeter of the tissue site that may remain in place for an extended time and allows an over-drape to be attached to it. The system and method further may include a manifold sized and configured to be placed in contact with the tissue site; the over-drape positioned over the manifold and sealed to the gasket to create a sealed space between the over-drape and the tissue site; and a reduced-pressure source fluidly coupled to the sealed space to deliver reduced pressure to the tissue site. A method is also presented.

9 Claims, 4 Drawing Sheets

Related U.S. Application Data of application No. 13/487,763, filed on Jun. 4, 2012, now Pat. No. 8,556,871, which is a division of application No. 12/195,115, filed on Aug. 20, 2008, now Pat. No. 8,211,071.

(60) Provisional application No. 60/965,755, filed on Aug. 21, 2007.

(51) Int. Cl.
*A61F 13/02* (2006.01)
*A61B 17/08* (2006.01)
*A61B 46/00* (2016.01)
*A61B 46/20* (2016.01)

(52) U.S. Cl.
CPC ......... *A61M 1/0086* (2014.02); *A61B 17/085* (2013.01); *A61B 46/00* (2016.02); *A61B 2046/205* (2016.02); *A61B 2217/005* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,562,107 A * | 10/1996 | Lavender | A61F 13/0269 128/888 |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 9,345,823 B2 * | 5/2016 | Mormino | A61M 1/0088 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0082059 A1 * | 4/2008 | Fink | A61M 1/0001 604/305 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |

(56) References Cited

FOREIGN PATENT DOCUMENTS

| WO | 93/09727 A1 | 5/1993 |
|---|---|---|
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

REDUCED-PRESSURE SYSTEM AND METHOD EMPLOYING A GASKET

CROSS-REFERENCE TO RELATED APPLICATIONS

This application is a divisional of U.S. patent application Ser. No. 14/025,271, filed Sep. 12, 2013, which is a divisional of U.S. patent application Ser. No. 13/487,763, filed Jun. 4, 2012, which is a divisional of U.S. patent application Ser. No. 12/195,115, filed Aug. 20, 2008, which claims the benefit under 35 USC §119(e) of the filing of U.S. Provisional Application No. 60/965,755, entitled "Reduced Pressure System Employing a Gasket Disposed Circumferentially Around a Tissue Site", filed Aug. 21, 2007. Each of the above applications are incorporated herein by reference for all purposes.

BACKGROUND

1. Field of the Invention

The present invention relates generally to medical treatment systems and in particular to a reduced-pressure system and method employing a gasket.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue.

In order to use reduced pressure on a tissue site, a pneumatic seal is achieved over the dressing using a semipermeable drape that is sealed to the patient's epidermis. In order to achieve this seal, an adhesive has been used at times or a sealing tape. At times, to help provide a better seal, healthcare providers have navigated the difficult task of using sealing material to form strips around the wound before placing the drape over the dressing and wound. With reduced-pressure therapy, a dressing is applied and usually is periodically changed. This typically means that the dressing is changed with some frequency—often three times a week or more. When such changes take place, the sealing tape is removed. This can cause irritation to the periwound region and pain to the patient.

It would be desirable to have a system and method that would allow for wound dressing changes with less pain for the patient and without requiring removal of all components of the system. It would also be desirable to provide a system that would be relatively easy to apply to a patient. Moreover, it would be desirable to have a system with a good pneumatic seal formed over the wound site.

SUMMARY

Problems with existing reduced-pressure systems and methods are addressed by the systems and methods of the illustrative embodiments described herein. According to one illustrative embodiment, a reduced-pressure treatment system for treating a tissue site on a patient includes a gasket releasably attached around a perimeter of the tissue site; a manifold sized and configured to be placed in contact with the tissue site; an over-drape positioned over the manifold and sealed to the gasket to create a sealed space between the over-drape and the tissue site; and a reduced-pressure source fluidly coupled to the sealed space to deliver reduced pressure to the tissue site. The gasket may be operable to remain in place for an extended time.

According to another illustrative embodiment, a method for treating a tissue site on a patient with reduced pressure includes the steps of: releasably attaching a gasket around a perimeter of the tissue site; placing a manifold in contact with the tissue site; disposing an over-drape over the manifold; sealing the over-drape to the gasket to create a sealed space between the over-drape and the tissue site; and providing reduced pressure to the sealed space to treat the tissue site.

The illustrative embodiment of the systems and methods of the present invention may provide for a number of perceived advantages. A few examples follow. Technical advantages of the present invention may include that system is relatively easy to apply. Another advantage is the system may be easier on the periwound region of the epidermis. Another advantage is that the patient may experience relatively reduced or eliminated pain associated with dressing changes. Another advantage is that the likelihood of pneumatic leak is decreased. These are only some examples.

Other objects, features, and advantages of the illustrative embodiments will become apparent with reference to the drawings and detailed description that follow

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
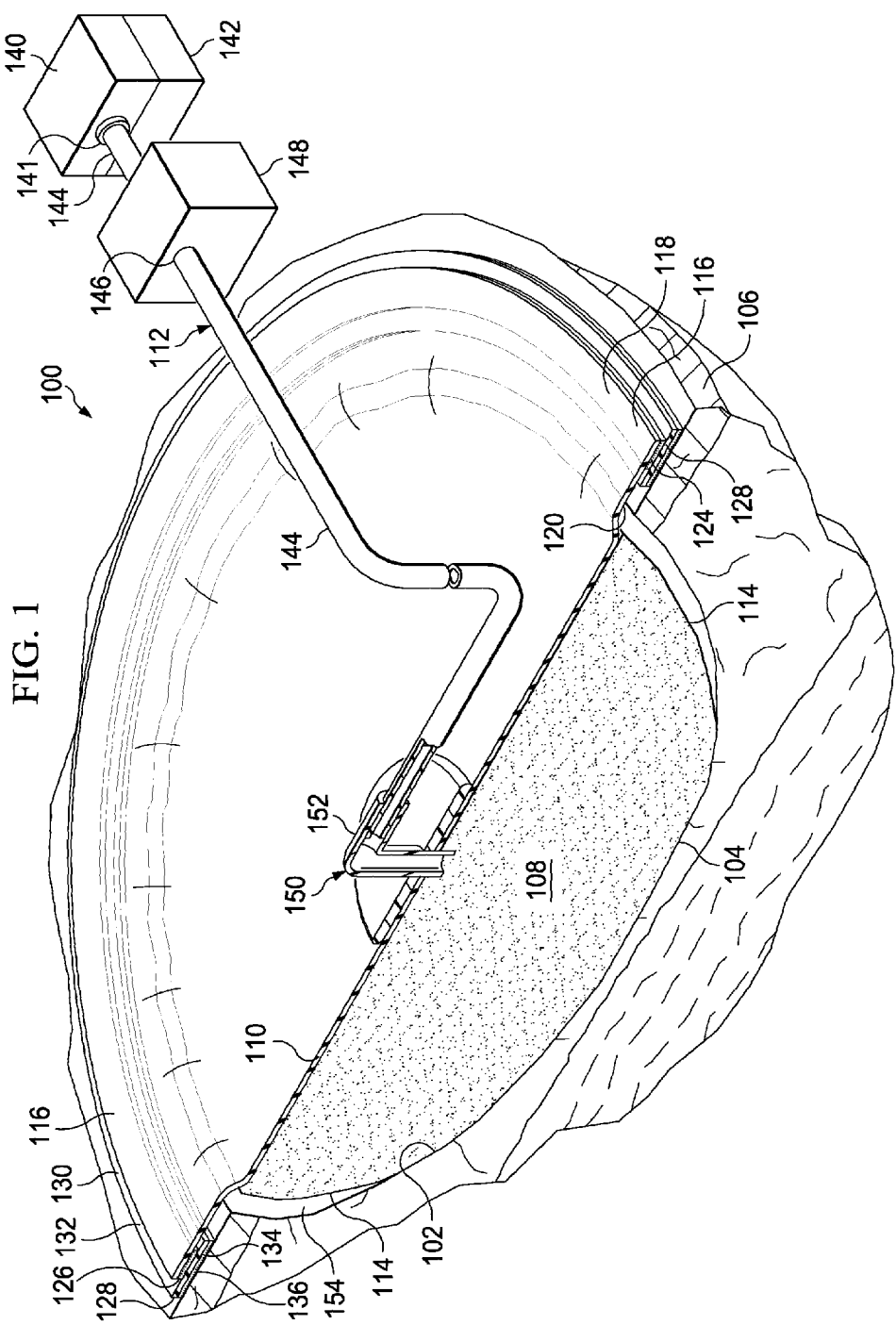
FIG. 1 is a schematic, perspective view with a portion in cross-section of an illustrative embodiment of a reduced-pressure system employing a gasket.

Referring to FIG. 1, an illustrative embodiment of a reduced-pressure treatment system 100 for treating a wound 102 at a tissue site 104, which is centered in a wound bed. System 100 may include a manifold member 108, or simply manifold; an over-drape 110; and a reduced-pressure subsystem 112. System 100 includes gasket 128.

In one illustrative embodiment, the manifold member 108 is made from a porous and permeable foam-like material and, more particularly, a reticulated, open-cell polyurethane or polyether foam that allows good permeability of wound fluids while under a reduced pressure. One such foam material that has been used is the VAC® Granufoam® Dressing available from Kinetic Concepts, Inc. (KCI) of San Antonio, Tex. Any material or combination of materials might be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam, such as open-cell foam, porous tissue collections, and liquids, gels, and foams that include or cure to include flow channels. The manifold material might also be a combination or layering of materials; for example, a first manifold layer of hydrophilic foam might be disposed adjacent to a second manifold layer of hydrophobic foam to form the manifold member 108.

The reticulated pores of the Granufoam® material, that are in the range of about 400 to 600 microns, are helpful in carrying out the manifold function, but again other materials may be used. A material with a higher, or lower, density (smaller pore size) than Granufoam® material may be desirable in some situations. The manifold member 108 may also be a reticulated foam that is later felted to thickness of about ⅓ its original thickness. Among the many possible materials, the following might be used: Granufoam® material or a Foamex technical foam (www.foamex.com). In some instances it may be desirable to add ionic silver to the foam in a microbonding process or to add other substances to the manifold member such as antimicrobial agents. The manifold member 108 could be a bio-absorbable material or an anisotropic material.

The over-drape 118 covers the manifold member 108 and extends past a peripheral edge 114 of the manifold member 108 to form a drape extension 116. Drape extension 116 has a first side 118 and a second, patient-facing side 120. Drape extension 116 may be sealed against a gasket 128 by sealing apparatus 124, such as an adhesive 126. Sealing apparatus 124 may take numerous forms, such as an adhesive sealing tape, or drape tape or strip; double-side drape tape; adhesive 126; paste; hydrocolloid; hydrogel; or other sealing means. If a tape is used, it may be formed of the same material as the over-drape 110 with a pre-applied, pressure-sensitive adhesive. Pressure-sensitive adhesive 126 may be applied on a second, patient-facing side 120 of drape extension 116. Adhesive 126 provides a substantially pneumatic seal between the over-drape 110 and the gasket 128. Before the over-drape 110 is secured to the patient, removable strips covering the adhesive 126 may be removed.

Over-drape 110 may be an elastomeric material that has pore sizes less than about 20 microns, but other materials and sizes might be used. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, over-drape materials may include a silicone, 3M Tegaderm® drape material, acrylic drape material, such as one available from Avery, or an incise drape material.

Gasket 128 has a gasket material 130 with a first side 132 and a second, patient-facing side 134. A second attachment apparatus 136 may be coupled to the second side 134 of the gasket material 130 for releasably attaching the gasket 128 to the patient's epidermis 106, or more generally skin. The gasket material 130 may be a thin polymer film, such as polyurethane, polyester, silicone, or a hydrocolloid, or could include any suitable gasket material. The second attachment apparatus 136 holding the gasket 128 in place may be a relatively water-resistant material, such as an Avery® brand Wet-stick adhesive, a colloid, acrylic, polyisobutylene (PIB), etc. The second attachment apparatus 136 allows the gasket 128 to be held in place for an extended time, e.g. one to two weeks or more, and then to be removed. The over-drape 110 may be re-attachable to the gasket 128 should the clinician find a need to view the wound and re-attach the over-drape 110. This allows the gasket 128 to stay in place for an extended time without significant agitation of the periwound area of the epidermis 106.

Reduced-pressure subsystem 112 includes a reduced-pressure source 140, which can take many different forms. Reduced-pressure source 140 provides a reduced pressure as a part of system 100. The term "reduced pressure" as used herein generally refers to a pressure less than the ambient pressure at a tissue site 104 that is being subjected to treatment. In most cases, this reduced pressure will be less than the atmospheric pressure at which the patient is located. Alternatively, the reduced pressure may be less than a hydrostatic pressure of tissue at the tissue site 104. It is often desirable for the reduced-pressure source 140 to develop a continuous reduced pressure below atmospheric pressure and also be able to deliver a dynamic pressure, i.e., to vary the reduced pressure in a cycle or operate in a continuous or intermittent mode. The operable range of reduced pressure may vary widely as needed, but would typically include 200 mm Hg below atmospheric. When one refers to increasing the reduced pressure, it typically refers to increasing the absolute value of the negative gauge pressure, and likewise, when one speaks of decreasing the reduced pressure, it typically means that the absolute value of the negative gauge pressure is decreasing.

In the illustrative embodiment of FIG. 1, reduced-pressure source 140 is shown having a reservoir region 142, or canister region. An interposed membrane filter, such as hydrophobic or oleophobic filter, might be interspersed between a delivery conduit, or tubing, 144 and the reduced-pressure source 140. A medial portion 146 of conduit 144 may have one or more devices, such as device 148. For example, the device 148 might be another fluid reservoir, or collection member to hold exudates and other fluids removed. Other examples of devices 148 that might be included on the medial portion 146 of delivery conduit 144 include pres sure-feedback devices, volume detection systems, blood detection systems, infection detection system, flow monitoring systems, temperature monitoring systems, etc. Some of these devices may be formed integral to the reduce-pressure source 140. For example, a reduced-pressure port 141 on reduced-pressure source 140 may include a filter member that includes one or more filters, e.g., an odor filter.

The reduced pressure developed by reduce-pressure source 140 is delivered through the delivery conduit 144 to a reduced-pressure interface 150, which might be an elbow port 152. In one illustrative embodiment, port 152 is a TRAC® technology port available from Kinetic Concepts, Inc. of San Antonio, Tex. Interface 150 allows the reduced pressure to be delivered through over-drape 110 and realized within sealed space 154. In this illustrative embodiment, elbow port 152 extends through over-drape 110 and into manifold member 108.

Figure 2:
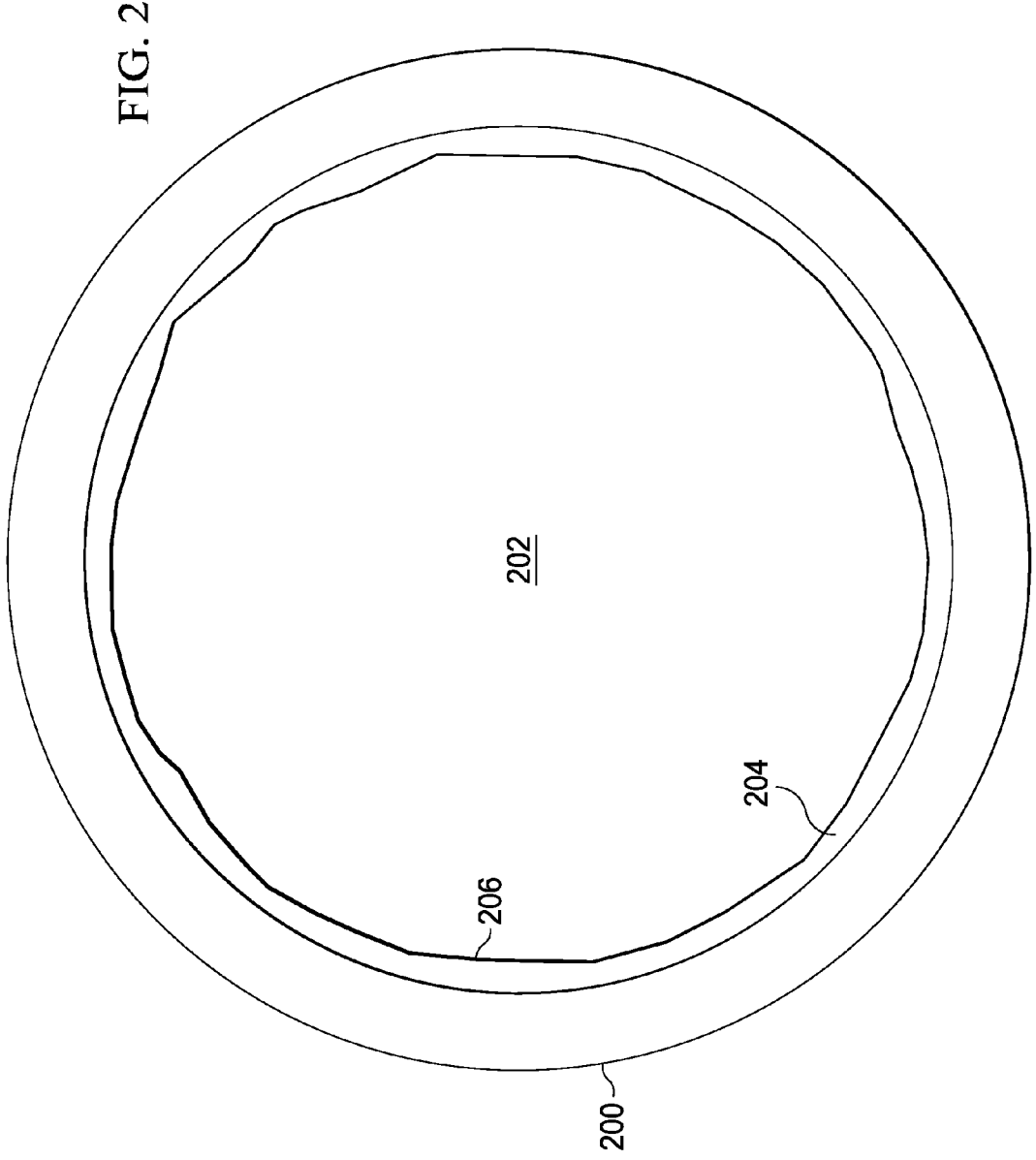
FIG. 2 is a schematic, plan view of an illustrative embodiment of a gasket disposed circumferentially around a tissue site.

Referring now to FIG. 2, an illustrative embodiment of a gasket 200 is shown disposed circumferentially about wound 202. A small margin 204 is shown at the wound edge 206. It will be appreciated from FIG. 2 that irregular shaped wounds, such as wound 202, should be accommodated. One way to accommodate the irregular shape is to attach gasket 200 using a gasket tape, i.e., a gasket material with attachment means that can be applied to the patient like a tape. In this regard, FIG. 3, shows an illustrative embodiment of a gasket tape dispenser 300.

Gasket tape dispenser 300 dispenses gasket 302, or gasket tape, which has a gasket material 304 and an attachment apparatus 306. The dispenser 300 may take many forms, but in this embodiment, contains a first chamber portion 308, which holds a roll of gasket tape 302. The healthcare provider can thus use the dispenser 300 to dispense gasket 302 about the perimeter of the tissue site proximate wound 310 on or through epidermis 311. To do so, the dispenser 300 is moved in the direction shown by arrow 314. In some instances, it may be desirable to include a releasable backing material on the attachment means 306 until it is ready for application; in such a situation, a second chamber 312 (shown in broken lines) may be included for collecting the removed backing material. The second chamber 312 may include a spring-loaded spindle that pulls the removed backing material on to it. There are numerous other ways the gasket 302 might be dispensed.

Figure 3:
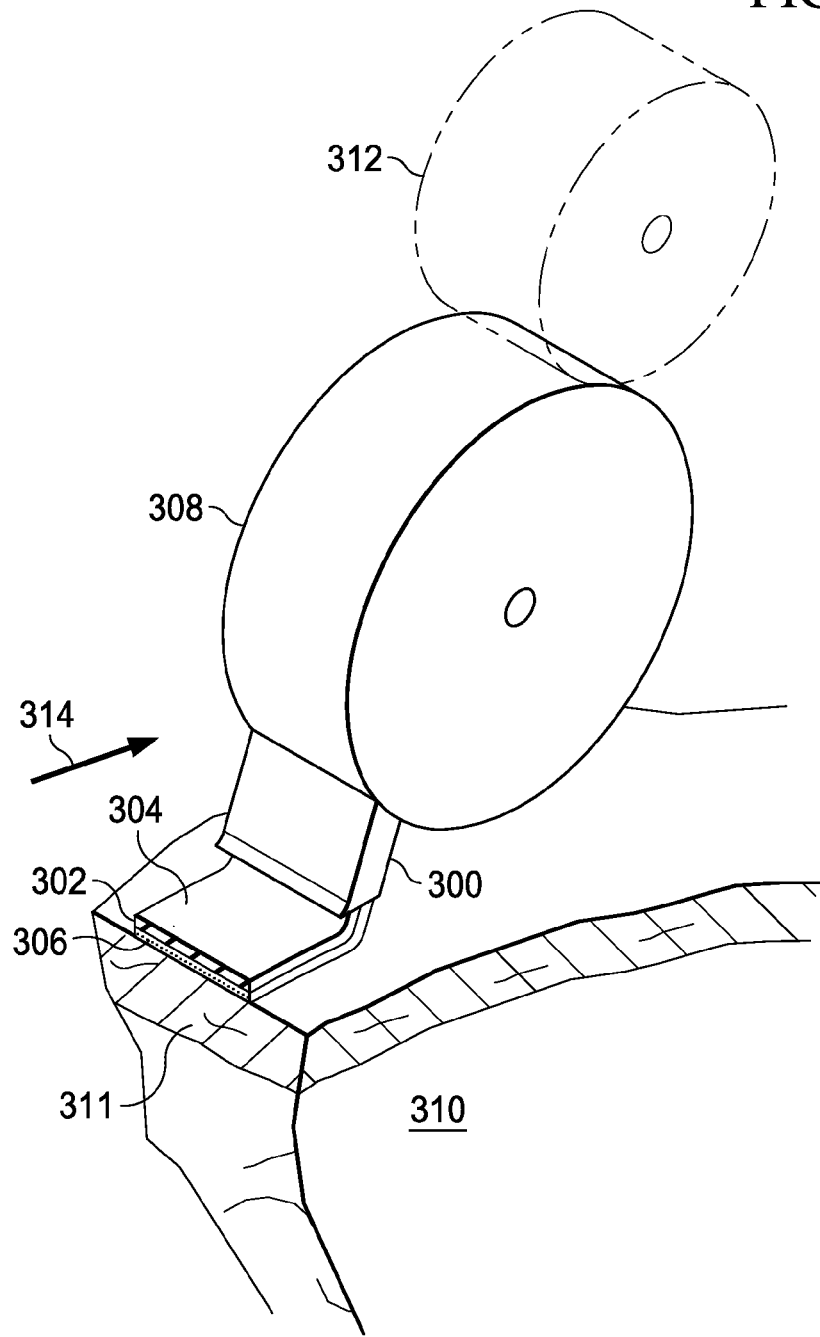
FIG. 3 is a schematic, perspective view of an illustrative embodiment of a dispenser for applying an illustrative gasket to a periwound area of a patient's epidermis.

Referring again to FIG. 2, in operation, the healthcare provider treating a wound 202 may, after appropriately cleaning and preparing the periwound region, apply a gasket 200 about the wound 202 using a dispenser, such as dispenser 300 in FIG. 3, or otherwise placing the gasket 200 proximate the wound 202. The gasket 200 provides a long-lasting perimeter about the wound 202 that facilitates attachment of an over-drape and that allows the over-drape to be removed without requiring the gasket 200 to be removed. By "long-lasting," it is meant that the gasket 200 could remain attached and operable for as long as one to two weeks or even longer.

Referring again to FIG. 1 and continuing consideration of one illustrative embodiment in operation, once the gasket 128 has been applied in a manner analogous to that just described for gasket 200 and the manifold 108 put in place, the over-drape 110 may be placed over the wound 102 and attachment apparatus 124 used to secure the over-drape 110 to the gasket 128 and in particular to releasably attach drape extension 116 to the gasket 128. In this instance, attachment apparatus 124 is an adhesive layer 126 and requires removal of a removable backing before application. Once over-drape 110 is sealed, it provides the pneumatically sealed space 154. The reduced-pressure interface 150 is applied through over-drape 110 to allow reduced pressure from reduced-pressure subsystem 112 to reach the manifold 108. The reduced-pressure subsystem 112 may be activated and reduced pressure supplied to manifold 108 in sealed spaced 154.

Figure 4:
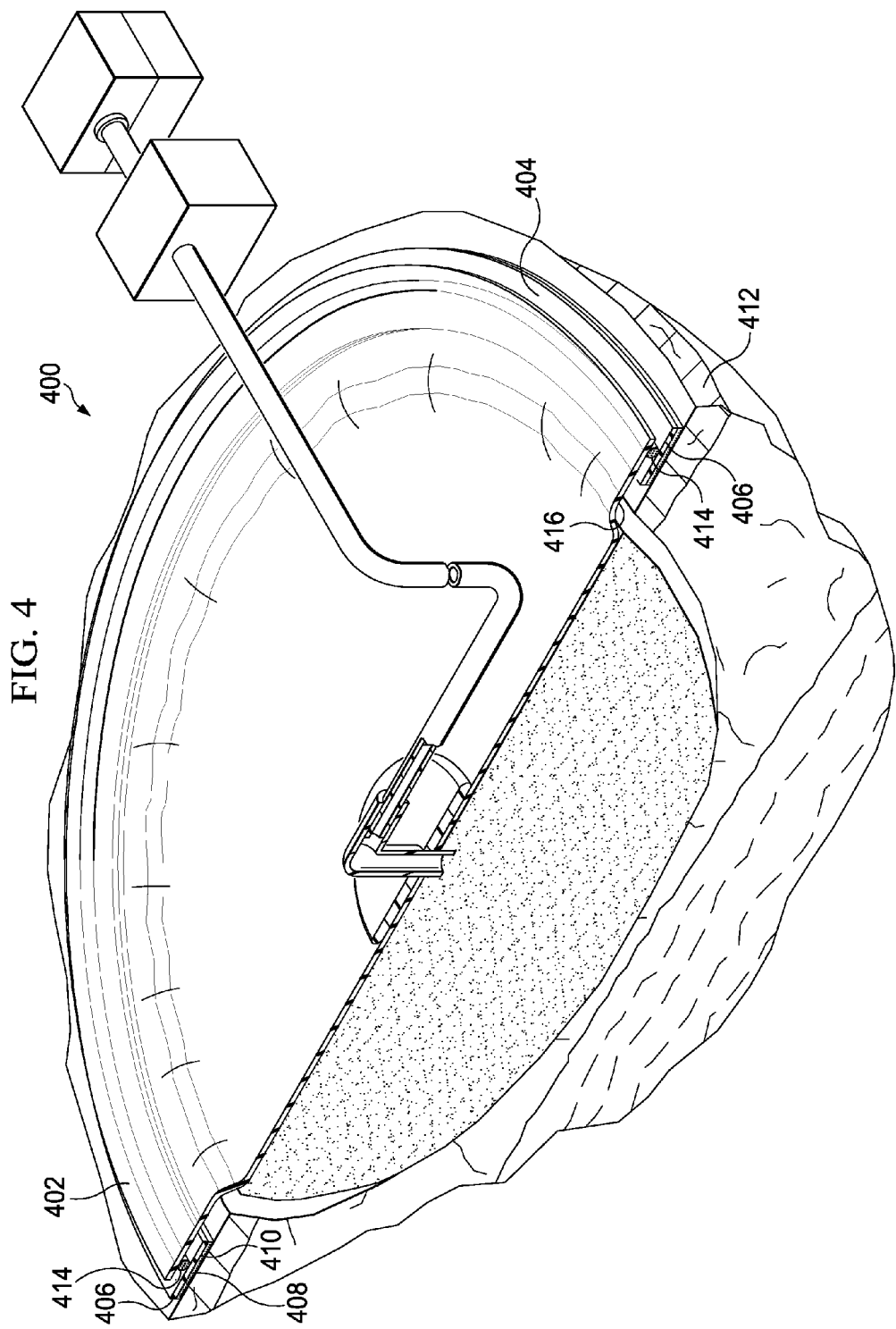
FIG. 4 is a schematic, cross-sectional view of a portion of an illustrative embodiment of a reduced-pressure system employing a gasket.

Referring now to FIG. 4, another illustrative embodiment for releasably sealing over-drape 402 to first side 404 of gasket 406 is shown. Gasket 406 has a sealing apparatus 408 on a second, patient-facing side 410 that holds and seals the gasket 406 in a long-lasting way to the patient's epidermis 412. In this illustrative embodiment, the over-drape 402 is secured using a bead 414 of adhesive applied to the first side 404 of the gasket 406 and against a second, patient-facing side 416 of over-drape 402. The bead 414 may be applied using an applicator similar to a caulk gun. In still another illustrative embodiment, a material capable of drying and adhering to a patient's epidermis periwound might be painted on or sprayed on and allowed to dry.

It should be apparent from the foregoing that an invention having significant advantages has been provided. While the invention is shown in only a few of its forms, it is not just limited but is susceptible to various changes and modifications without departing from the spirit thereof.

What is claimed is:

1. A system adapted for assembly to treat a tissue site, comprising:
   a manifold adapted for placement proximate to the tissue site;
   a gasket adapted for placement on a periwound area around the tissue site;
   an over-drape adapted to cover the manifold and to extend past a peripheral edge of the manifold to form a drape extension;
   a first attachment apparatus comprising a first adhesive adapted for application between the drape extension and the gasket; and
   a second attachment apparatus comprising a second adhesive adapted for application between the gasket and the periwound area;
   wherein the first attachment apparatus is weaker than the second attachment apparatus;
   wherein the first adhesive is different from the second adhesive.

2. The system of claim 1, wherein the gasket comprises a thin polymer film having a first side and a second, patient-facing side, and wherein the first attachment apparatus is adapted to be positioned on the first side of the gasket and the second attachment apparatus is adapted to be positioned on the second, patient-facing side of the gasket.

3. The system of claim 2, wherein the thin polymer film comprises polyurethane.

4. The system of claim 2, wherein the thin polymer film comprises polyester.

5. The system of claim 1, wherein the first attachment apparatus is separated from the second attachment apparatus by the gasket.

6. The system of claim 1, wherein the second attachment apparatus comprises an adhesive tape.

7. The system of claim 1, wherein the first attachment apparatus comprises a pressure-sensitive adhesive.

8. The system of claim 1, wherein the first attachment apparatus comprises a bead of adhesive.

9. The system of claim 1, wherein the gasket comprises a hydrocolloid.

* * * * *